US006258321B1

(12) United States Patent
Van Driel et al.

(10) Patent No.: US 6,258,321 B1
(45) Date of Patent: Jul. 10, 2001

(54) APPARATUS AND METHOD FOR CARDIOPLEGIA DELIVERY

(75) Inventors: Michael R. Van Driel, Fountain Valley; Russell Joseph, Las Flores, both of CA (US)

(73) Assignee: Dideco S.p.A. (IT)

( * ) Notice: Subject to any disclaimer, the term of this patent is extended or adjusted under 35 U.S.C. 154(b) by 0 days.

(21) Appl. No.: 09/305,941

(22) Filed: May 6, 1999

(51) Int. Cl.[7] .............................. A61M 1/14; A61M 1/34; A61M 1/36; B01D 39/14

(52) U.S. Cl. .............................. 422/44; 422/48; 604/6.09; 604/6.14; 210/500.23; 210/500.36; 96/10

(58) Field of Search ............................ 604/4.01, 26, 6.09, 604/6.13, 6.14; 422/44, 45, 48; 428/372, 376, 389; 210/321.89, 352, 500.23, 500.36; 264/41, 49; 96/6, 10

(56) References Cited

U.S. PATENT DOCUMENTS

| | | |
|---|---|---|
| Re. 36,125 | 3/1999 | Haworth et al. . |
| 3,794,468 | 2/1974 | Leonard . |
| 4,572,446 | 2/1986 | Leonard et al. . |
| 4,666,543 | 5/1987 | Kawano . |
| 4,975,247 | 12/1990 | Badolato et al. . |
| 5,137,531 | 8/1992 | Lee et al. . |
| 5,162,101 | 11/1992 | Cosentino et al. . |
| 5,297,591 | 3/1994 | Baurmeister . |
| 5,429,184 | 7/1995 | Bach et al. . |
| 5,706,889 | 1/1998 | Bach et al. . |
| 5,718,869 | 2/1998 | Bach et al. . |
| 5,817,279 | 10/1998 | Eilers et al. . |
| 5,830,370 | 11/1998 | Maloney, Jr. et al. . |
| 5,837,033 * | 11/1998 | Giglia et al. . |
| 6,001,306 | 12/1999 | McFall et al. . |
| 6,113,782 * | 9/2000 | Leonard . |

OTHER PUBLICATIONS

International Search Report for PCT/US00/12482.

* cited by examiner

*Primary Examiner*—Angela D. Sykes
*Assistant Examiner*—Patricia Bianco
(74) *Attorney, Agent, or Firm*—Popovich & Wiles, P.A.

(57) ABSTRACT

An apparatus and a method for making a transfer device comprising a tube bundle. The transfer device is suitable for use as a heat exchanger in a blood cardioplegia circuit, for example. The apparatus axially winds a flexible tube around a winding core. The apparatus includes a winding core, a core rotating means, a tube bobbin, and a tube shuttle to guide the tube around the core. A shuttle rotating means rotates the tube shuttle around the core. The method of making the transfer device includes providing a winding core, winding a tube from end to end around the winding core, fitting the wound bundle into a housing, sealing the first and second ends of the housing using a potting material, cutting the ends of the bundle to expose a lumen within the tubes, and attaching a first end cap and a second end cap.

14 Claims, 13 Drawing Sheets

10 12 14 15 16 17 18 19

10
21
20
29
26
29
28
30
1
22

31
35
36
10
26
33
34
30
22
38
37
39

110
120
121
126
129
131
130
123
122

APPARATUS AND METHOD FOR CARDIOPLEGIA DELIVERY

FIELD OF THE INVENTION

The invention relates to a cardioplegia delivery device and method of its use to deliver either warm or cold cardioplegia fluids to the heart. More particularly, the invention is directed to an apparatus and method of using a cardioplegia delivery device having a wound fiber bundle.

BACKGROUND OF THE INVENTION

The use of hollow fiber bundles as mass transfer devices and energy transfer devices in the field of medical technology is well-known. For example, wound hollow fiber bundles have been used as blood oxygenators and dialyzers. The typical winding pattern for hollow fiber bundles can be described as a helical wind, where the tubes are wrapped around a rotating cylinder. One such winding technique is described in U.S. Pat. No. 4,975,247 by Badolato et al., which describes the means by which to wind a hollow fiber oxygenator with specialized winding equipment. Badolato et al. describes winding a single fiber or fiber ribbon onto a rotating core using a fiber guide which reciprocates along a line parallel to the axis of the core. The fiber is deposited spirally around the core as the fiber guide reciprocates and the core rotates.

Typical winding techniques such as that described in the Badolato patent are limited to large, for example, 2.0 inch diameter cores. If the core is smaller, the fiber will slide off of the core as the tubing is wound. If the core has a 2.0 inch or larger diameter, contact surface friction will maintain the fiber in place as the fiber is wound. Unfortunately, the relatively large diameter results in a larger priming volume which is undesirable for most medical applications. The increased priming volume results in increased levels of hemodilution which can be deleterious to the patient. In certain instances, the increased priming volume can prohibit the use of the device on smaller adults and children.

Alternatively, hollow fiber bundles may be wound with fiber mats which are not subject to the winding problems of fibers or fiber ribbons, discussed above. Specifically, neither core diameter nor the specific angle at which fibers must be wound around the core to maintain the fiber's position relative to the central axis of the core are factors when using woven fiber mats. As a matter of fact, when a fiber bundle is made using a fiber mat the bundle can be formed around a core with a relatively small diameter and the fibers can be substantially parallel to the axis of the core. However, fiber mats are expensive because of the additional complexities of the weaving process. Further, weaving typically precludes the direct cost control over the manufacturing process that exists when a bundle is wound from a single fiber or fiber ribbon. Therefore, it would be desirable to have a winding technique and apparatus which combines low cost, low prime volume and direct control over production without the disadvantages associated with present winding techniques or wound fiber mat device designs.

SUMMARY OF THE INVENTION

In one aspect, the invention is a transfer device. The transfer device includes a wound tube bundle, a housing, a potting material, a first fluid inlet, a first fluid outlet, a second fluid inlet and a second fluid outlet.

The wound tube bundle includes a plurality of tubes. Each of the tubes has an outer surface and a lumen. The plurality of tubes is derived from a tube being wound around a winding core and then cut to divide the original tube into a plurality of tubes. The tubes can be a microporous membrane hollow fiber. Suitable materials for the tubes may include cuprammonium rayon, viscose rayon, cellulose acetate, polyvinyl alcohol, ethylene vinyl alcohol, polysulfone, polypropylene or polymethyl-methacrylate. The winding core has a body, a first winding disk and a second winding disk. The first winding disk is attached to a first end of the body and a second winding disk is attached to a second end of the body. The winding core may also have a first cutting pad attached to the first winding disk and a second cutting pad secured to the second winding disk. The first and second winding disks have a peripheral edge and a central axis that substantially coincide with a longitudinal axis of the winding core. A plurality of fins extend from the peripheral edge of the winding disks towards the central axis. The fins define a plurality of primary notches which secure the plurality of tubes. The housing surrounds the wound tube bundle and has a first end and a second end. The potting material is disposed at the first and second ends of the housing. The potting material seals the first and second ends of the wound tube bundle to the housing. The potting material, the outer surface of the tubes and the housing cooperate to form a first fluid chamber. A first fluid inlet and first fluid outlet communicate with the first fluid chamber. A second fluid inlet communicates with the lumen of the plurality of tubes at the first end of the housing. A second fluid outlet communicating with the lumen of the plurality of tubes at the second end of the housing.

The fins can also define a plurality of secondary notches shaped to receive tube from the tube shuttle. The primary and secondary notches each having a length measured from the peripheral edge towards the central axis. The length of the primary notches being greater than the length of the secondary notches. The fins can also define a plurality of tertiary notches shaped to receive tube from the tube shuttle. The tertiary notches also have a length as measured from the peripheral edge towards the central axis. The length of the tertiary notches is less than the length of the secondary notches.

In a second aspect, the invention is a transfer device. The transfer device includes a wound tube bundle, a housing, a potting material, a first fluid inlet, a first fluid outlet, a second fluid inlet, and a second fluid outlet.

The wound tube bundle has a plurality of tubes, as described above. The winding core has a body, a first winding disk and a second winding disk. The first winding disk is attached to the first end of the body and the second winding disk is attached to the second end of the body. The winding core can also include a first cutting pad secured to the first winding disk and a second cutting pad secured to the second winding disk. The first and second winding disks have a diameter greater than a diameter of the body. Winding tube onto the winding core forms a space between the diameter of the body and the diameter of the first and second winding disks. The housing, potting material, first fluid inlet, first fluid, second fluid inlet and second fluid outlet are as described above.

In a third aspect, the invention is a method for manufacturing a transfer device. The method includes providing a winding core, winding a tube from end to end around the winding core, fitting the wound bundle into a housing, sealing the first and second ends of the housing using a potting material, cutting the ends of the bundle to expose a lumen within the tubes, and attaching a first end cap and a second end cap.

The winding core has a body, a first winding disk attached to a first end of the body and a second winding disk attached to a second end of the body. The first and second winding disks have a peripheral edge and a central axis that substantially coincides with a longitudinal axis of the winding core. The first and second winding disks further have a plurality of fins extending from the peripheral edge towards the central axis, the fins defining a plurality of primary notches shaped to receive tube. The housing is shaped to accept the tube bundle. The housing has a first end, a second end, a first fluid inlet and a first fluid outlet. The potting material is disposed at the first and second ends of the housing such that the potting material, the outer surface of the tubes and the housing form a first fluid chamber. The first fluid inlet and the first fluid outlet communicate with the first fluid chamber. The first end cap having a second fluid inlet attached to the first end of the housing communicates with the lumen of the tubes at the first end of the housing. The second end cap having a second fluid outlet attached to the second end of the housing communicates with the lumen of the tubes at the second end of the housing.

In a fourth aspect, the invention is a method for manufacturing a transfer device. The method includes providing a winding core, described hereinafter, and winding a tube from end to end around the winding core, fitting the wound bundle into a housing, sealing the first and second ends of the housing, cutting the ends of the bundle to expose a lumen within the tubes, and attaching a first end cap and a second end, as described above.

The winding core has a body, a first winding disk attached to a first end of the body and a second winding disk attached to a second end of the body. The first winding disk and the second winding disk being shaped to accept tube and having a diameter greater than a diameter of the body.

In a fifth aspect, the invention is a method for manufacturing a transfer device. The method includes winding a tube bundle by providing a winding core, winding a row of a tube around the winding core substantially parallel to the winding core's longitudinal axis while the winding core is essentially stationary, incrementally rotating the winding core, winding a second row of tube around the winding while the winding core is essentially stationary, incrementally rotating the core and winding rows of the tube sequentially until a desired number of rows are wound around the winding core. Then fitting the wound bundle into a housing, sealing the first and second ends of the housing using a potting material, cutting the ends of the bundle to expose a lumen within the tubes; and attaching a first end cap and a second end cap, as described above.

In a sixth aspect, the invention is a method for manufacturing a transfer device. The method includes providing a winding core, winding a tube from end to end around the winding core, fitting the wound bundle into a housing having a first end and a second end, sealing the first and second ends of the housing using a potting material, cutting the ends of the bundle through the first and second cutting pads to expose a lumen within the tubes, and attaching a first end cap and a second end cap.

The winding core has a body, a first cutting pad attached to a first end of the body and a second cutting pad attached to a second end of the body. The first cutting pad and the second cutting pad being shaped to receive tube. The housing, potting, cutting, first fluid inlet, first fluid outlet, first end cap and second end cap are as described above.

DETAILED DESCRIPTION OF THE PREFERRED EMBODIMENTS

The method and winding device of the present invention can be used to make hollow tube or tube bundles for various medical applications which utilize a mass transfer device or an energy transfer device. The term "transfer device", as used herein, is meant to be inclusive of mass transfer and energy transfer applications. These applications include but are not limited to blood oxygenators, dialyzers, and heat exchangers. The term "tube", as used herein, is meant to be inclusive of all tubing, hollow fiber, or other flexible conduit known to those skilled in the art. The tube bundle formed in the described embodiment is suitable for use as a heat exchanger in a blood cardioplegia circuit and the dimensions, tubing, surface area, and other particulars provided in the specification are suitable therefore. The use of this method for constructing a tube bundle for other applications may involve the use of tubes having different dimensions, specifications and materials but the basic principles are the same.

Figure 1:
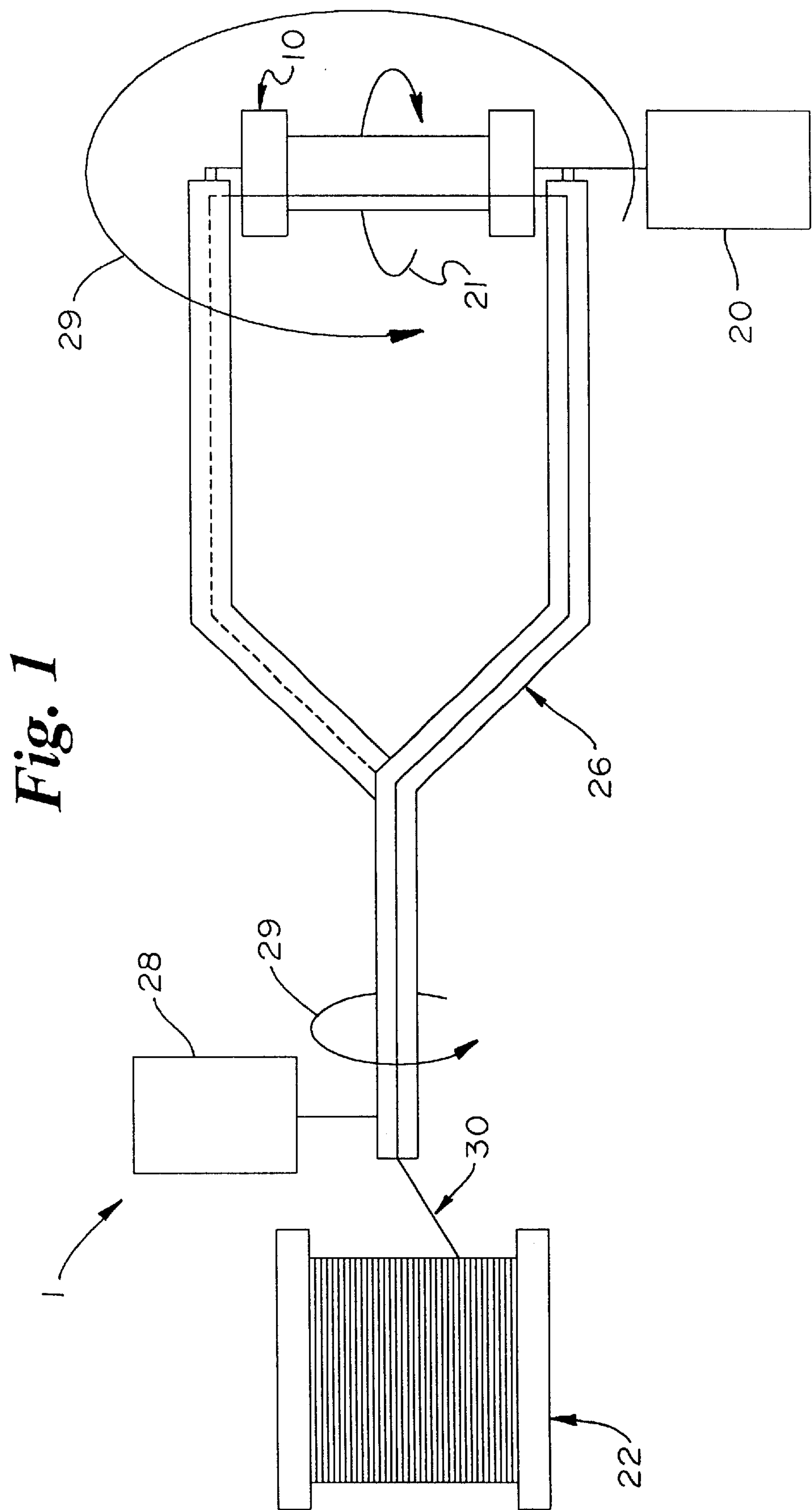
FIG. 1 is a schematic diagram of an embodiment of winding apparatus according to the present invention.

The apparatus and method for manufacturing a tube bundle of the present invention can be understood generally by reference to FIG. 1. FIG. 1 shows a winding apparatus designated generally as 1. Winding apparatus 1 axially winds a flexible tube 30 around a winding core 10. The winding apparatus includes: a winding core to accept tube 30, a core rotating means 20 for rotating core 10 in the direction of arrow 21, a tube bobbin 22 from which tube 30 is drawn, a tube shuttle 26 which 10 guides tube 30 around core 10, and a shuttle rotating means 28 which rotates tube shuttle 26 around core 10 in the direction of arrow 29.

In the finished tube bundle, tube 30 will carry a fluid within its lumen from one end of the tube bundle to the other end. Tube 30 may be any biocompatible material flexible enough for winding but is typically polyurethane for heat exchange applications. For blood oxygenators or dialyzers tube 30 would be a hollow fiber membrane as known in the art. For a cardioplegia heat exchanger, tube 30 may have an outside diameter of 0.01 to 0.10 inches and a wall thickness of 0.001 to 0.050 inches but preferably has an outside diameter of 0.030 to 0.045 inches and a wall thickness of 0.002 and 0.005 inches. Tube bobbin 22 holds tube 30 before tube 30 is wound onto winding core 10. Tube bobbin 22 holds a sufficient length of tube to continuously and completely wind core 10. Tube bobbin 22 is rotatably mounted such that tube 30 can be drawn off of bobbin 22. Tube 30 can be passively drawn off bobbin 22 or can be assisted by a means for rotating the bobbin such as a bobbin motor, shown in FIG. 7. Tube 30 is threaded from tube bobbin 22 through tube shuttle 26. Tube shuttle 26 may be a hollow tube appropriately angled to guide the tube as it is wound about core 10 in a manner described in more detail hereafter. The tube is then connected to winding core 10 in a manner discussed in more detail hereinafter. Tube shuttle 26 is shaped so as to wind tube 30 onto core 10 when tube shuttle 26 is rotated. Shuttle rotating means 28 rotates tube shuttle 26 around an axis substantially perpendicular to the core's axis thereby drawing tube 30 from bobbin 22 and winding tube 30 onto core 10. Shuttle rotating means 28 is preferably a stepper motor controlled by a micro-stepper drive. Tube shuttle 26 rotates about an axis substantially perpendicular to and intersecting the core's axis. The rotation of tube shuttle 26 around core 10 axially winds tube 30 onto core 10. To distribute tube 30 around core 10, core 10 is rotated an incrementing angle or distance after each rotation of the shuttle around the core. Rotation of the core by this incrementing angle or distance aligns the periphery of core 10 to accept another wind of tube 30 from tube shuttle 26. Thereby, in the next rotation, tube shuttle 26 winds a tube which is typically adjacent to the earlier wound tube and which is substantially parallel to both the earlier wound tube and the axis of core 10. The incrementing angle used will depend upon the particular tube and core design used in the bundle. Core 10 is rotated by core rotating means 20 about the core's longitudinal axis in a plane substantially perpendicular to the tube shuttle's rotational axis. Core rotating means 20 is preferably a stepper motor controlled by a micro-stepper drive.

Figure 2:
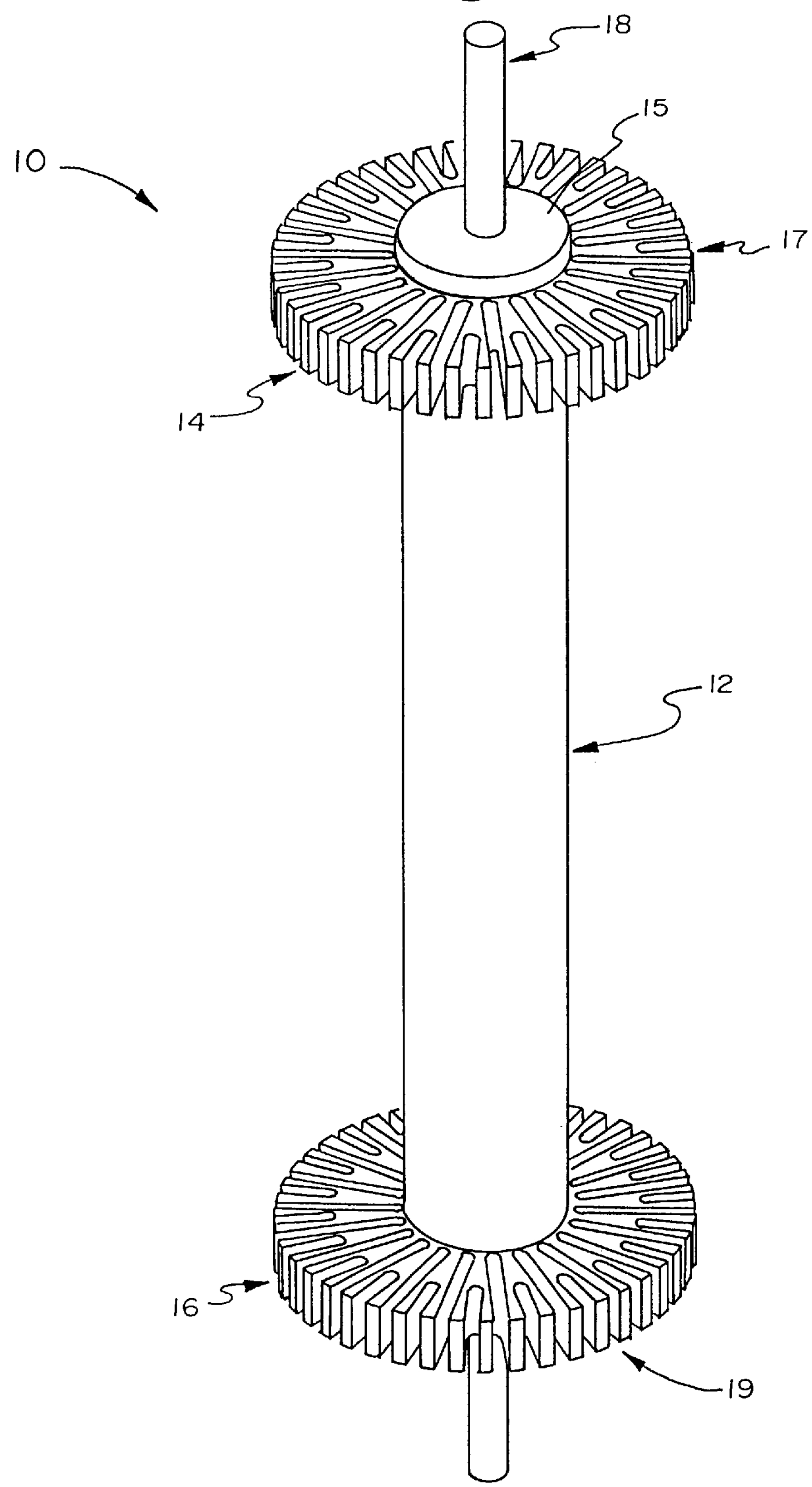
FIG. 2 is an isometric view of an embodiment of the winding core.

FIG. 2 shows an embodiment of winding core 10. Winding core 10 is shaped to accept and hold tubing from the tube shuttle but is typically cylindrical. Winding core 10 can be made from any material of sufficient strength to withstand the stress of the winding process but is preferably made from a rigid thermoplastic. Winding core 10 comprises a body 12 disposed between a first winding disk 14 and a second substantially identical winding disk 16. The winding disks generally lie within a plane perpendicular to the long axis of the body. The winding disks hold the tube as it is wound around core 10. Typically, the winding disks are circular and have a larger diameter than body 12. For tube bundles used in cardioplegia heat exchangers, the winding disks preferably have a diameter of greater than 1.0 inch. It is possible to use a winding disk with an outside diameter of up to about 3.0 inches although for most modem medical applications this results in prohibitively high priming volumes.

As shown in FIG. 2, the winding disks can optionally have fins 17 extending radially from the winding disks' outer periphery. Fins 17 provide more control over the pattern of tube during winding by holding the rows of the tube in position during winding and potting. The added control provided by the fins allows better regulation of the bundle size and subsequent priming volume for specific applications. Further, the added control contributes to improved device performance consistency and manufacturing repeatability. The tube can be positioned with a greater consistency than that of the other winding processes. Each two consecutive fins define a notch 19 therebetween. Notches 19 guide and hold the tube in place on core 10 during winding and other manufacturing steps as discussed hereafter. The point within a notch closest to the axis of core 10 is the inner diameter of the notch. The point within a notch furthest from the axis of core 10 but still between two fins is the outer diameter of the notch. The finned winding disks preferably have an inner notch diameter of greater than 0.25 inches and an outer notch diameter of less than 2.5 inches for winding cores used in cardioplegia heat exchangers. Fins 17 are spaced so as to accept a particular diameter of tube within the notches. The spacing between fins 17 can be varied so that notches 19 will accept the appropriate sized tube depending on the final application for the tube bundle.

During winding, creases can form as the tube bends around the winding disks. A cutting pad 15, shown in FIG. 2, can be placed on each end of the core to prevent the creases from constricting the lumen of the finished tube bundle. The cutting pads are extensions of the core which support the tube as the tube is wound. The added support moves the point at which the tubes crease outward beyond the winding disks. Thereby, the cutting pads enable the cutting of the tube beyond the constriction in the lumen caused by the crease without having to cut below or through the winding disks. Cutting pads 15 can be the circular disk shape, shown in FIG. 2, or can have the same shape as the winding disk and fins, not shown. When the cutting pads have the same shape as the winding disk and fins, the cutting pads can extend along the fins a distance up to the outer notch diameter and are configured to allow the tube to fit within the notches. Cutting pads 15 typically extend about 0.16 inch from the end of the winding core. Pads 15 can be co-molded into the winding core or can be bonded to the ends of the core after molding. The pad is preferably made of a low durometer material, typically having a shore hardness of 50A to 70D, so as not to damage the blade during cutting.

A winding pin 18, shown in FIG. 2, extends through the end of a long axis of body 12 protruding through first winding disk 14 and second winding disk 16. Winding pin 18 is shaped so as to be secured to the core rotating means and facilitate winding. Winding pin 18 can be a single dowel extending through core 10. Alternatively, winding pin 18 can be integrally molded from the material of core 10. Winding pin 18 should be formed from a material having sufficient strength to support core 10 during the winding process but, is typically a suitable metal or polyurethane. Winding pin 18 can be connected to the winding apparatus by either one or both ends.

Figure 3:
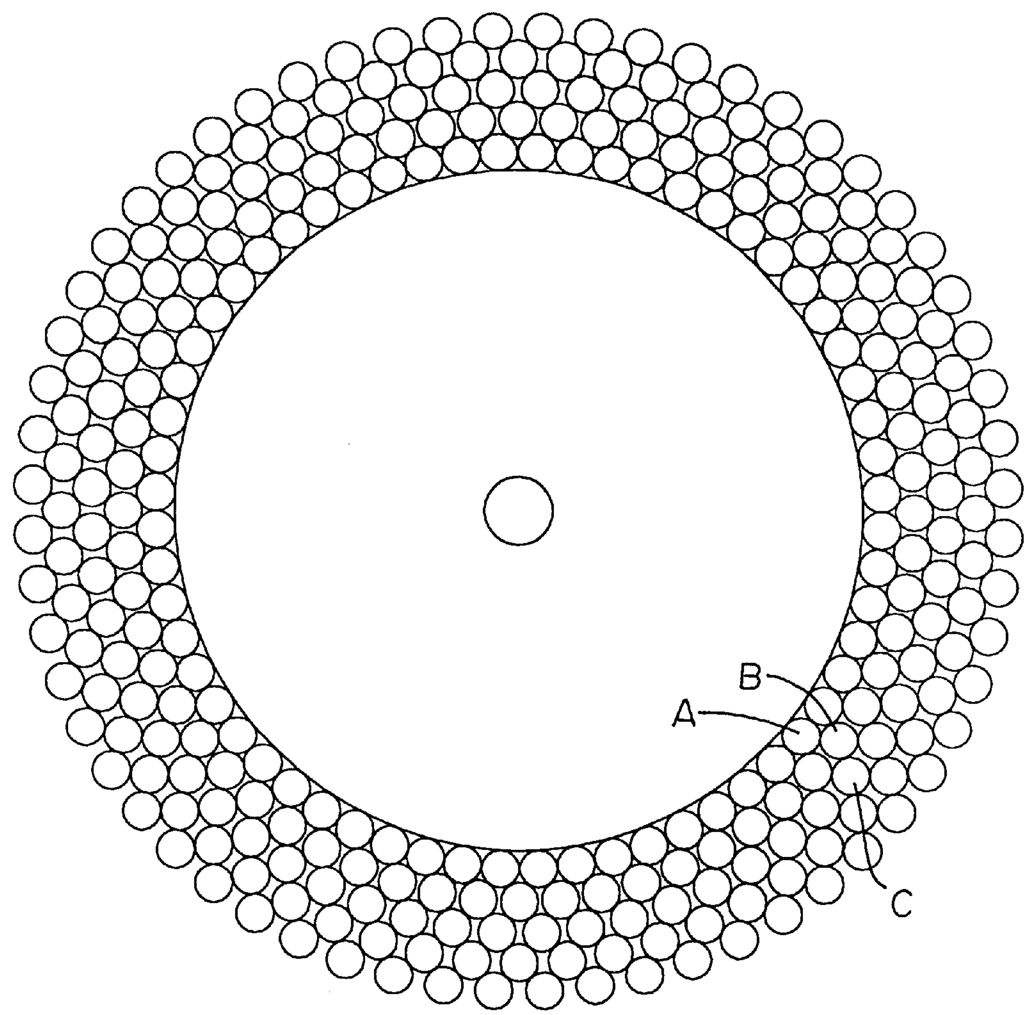
FIG. 3 is a cross-sectional view of the unfinned winding disk of an embodiment of the winding core with tubes.

FIG. 3 shows a cross-sectional view along the outer surface of a winding disk after winding has been completed. FIG. 3 exemplifies a tube winding pattern which can result from winding a core without fins. As layer A is wound onto the core each row of tube within the layer nestles against the adjacent row of tube. Winding of rows within a layer continues until the layer is complete. A layer is completed when rows have been wound 360 degrees around the perimeter of the winding disks. Subsequent layers can be added over prior layers by winding additional rows of tube over the prior layers. In the unfinned design, subsequent layers B, C . . . N nestle in the groove created between the tubes of the prior layer. As additional layers are added, the spacing between the tubes of subsequent layers increases relative to the spacing between the rows of the prior layers, thereby, increasing the distance between the rows of tube in the subsequent layer. Using this configuration, a winding core having winding disks with, for example, a diameter of 0.90 inches can be wound with 40 rows of 0.040 inch diameter polyurethane tubing to a maximum of eight layers. Using these parameters, a total of 300 cut tubes will be in the completed tube bundle. In the above example, the rows in the first layer are not biased against one another but, instead, are spaced evenly around the winding disk.

Figure 4:
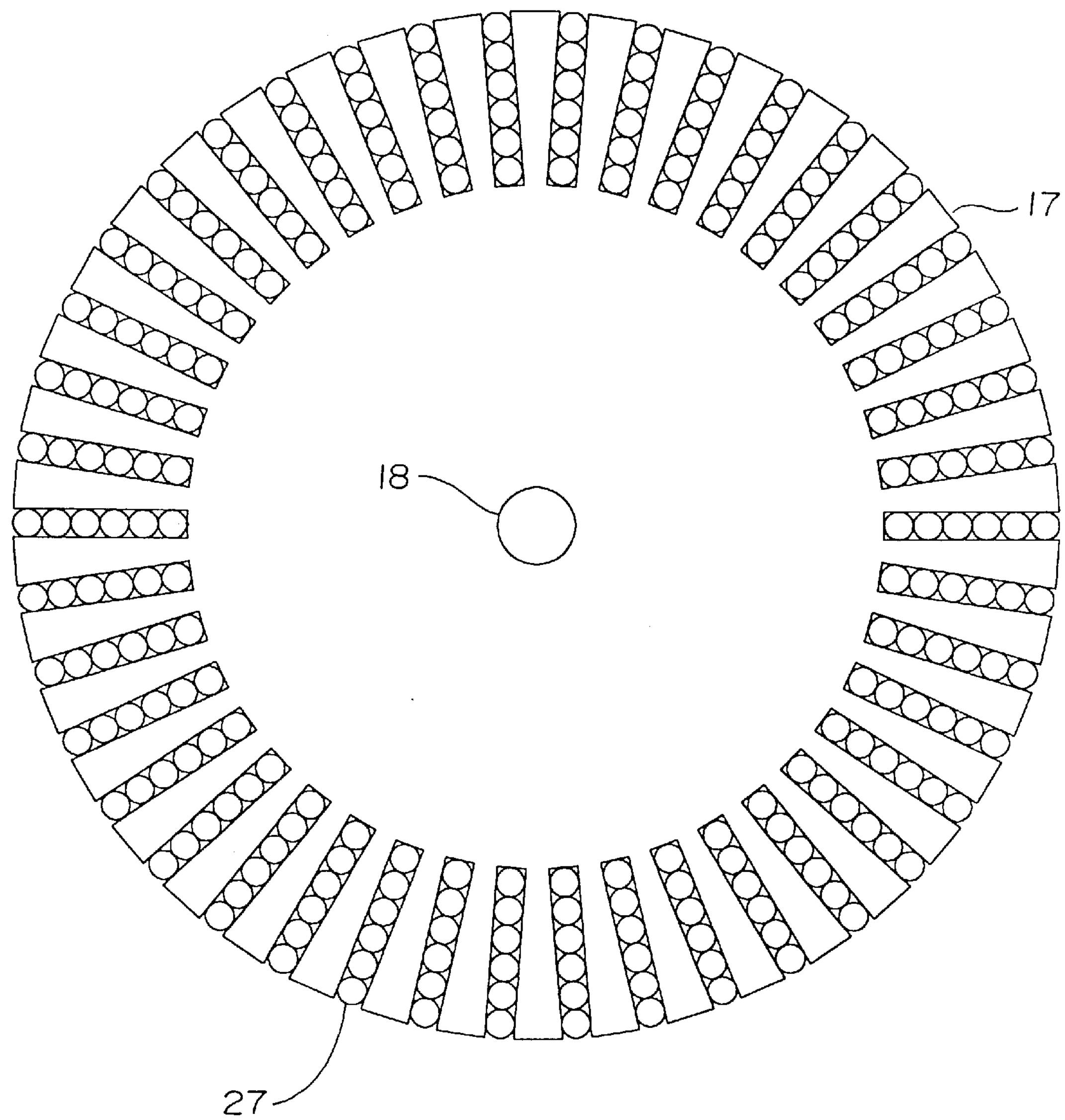
FIG. 4 is an end view of the finned winding disk of an embodiment of the winding core.

FIG. 4 shows an end view of a winding disk with fins in a one-layer fin design. The fins define primary notches 27 as the space between each two consecutive fins. The fins guide the tube into primary notches 27 as the tube is wound around the core. Thus, the fins represent an improvement over the design of FIG. 3 since the fins help locate the tube during the winding process. Further, the fins allow winding on a winding core having a smaller inside diameter. The fins should be sufficiently thick so as to prevent stress fractures during molding of the core or breakage during manufacture of the wound tube bundle. Typically, the thickness should be no less than 0.02 inches for application in cardioplegia heat exchangers. This minimum thickness also prevents moldability issues from arising, like for example, the potential for warping and formation of sink holes during cooling.

During winding of the one layer fin design, two rows of tube 30 are deposited for each complete rotation of tube shuttle 26 around winding core 10. The tube shuttle deposits the two rows of tube 30 on substantially diametrically opposite sides of the winding disk. After each rotation of the tube shuttle around the core, the core is rotated by an incrementing angle. The incrementing angle is the angular displacement of the core and determines the location where the next two rows of tube will be placed. For a winding core having a winding disk as in FIG. 4, the incrementing angle is chosen so that the core rotates a distance sufficient to allow the next winding cycle to deposit a tube in the next notch or next desired multiple of notches. A layer around a finned winding core is completed after the winding apparatus has deposited tube 30 in all notches around the 360 degree perimeter of the winding disks. Additional layers are then added by placing additional rows in the notches over the rows in the prior layer. Thus, rows in subsequent layers butt against corresponding rows in the prior layers the rows extending radially outward from the axis of the core.

Using the fin design of FIG. 4, a winding core having winding disks with an outer diameter of 1.6 inches, typical for cardioplegia heat exchangers, can be wound with 42 rows of 0.040 inch diameter polyurethane tubing to a maximum of six layers. Using these parameters, a total of 252 cut tubes will be in the complete tube bundle.

Figure 5:
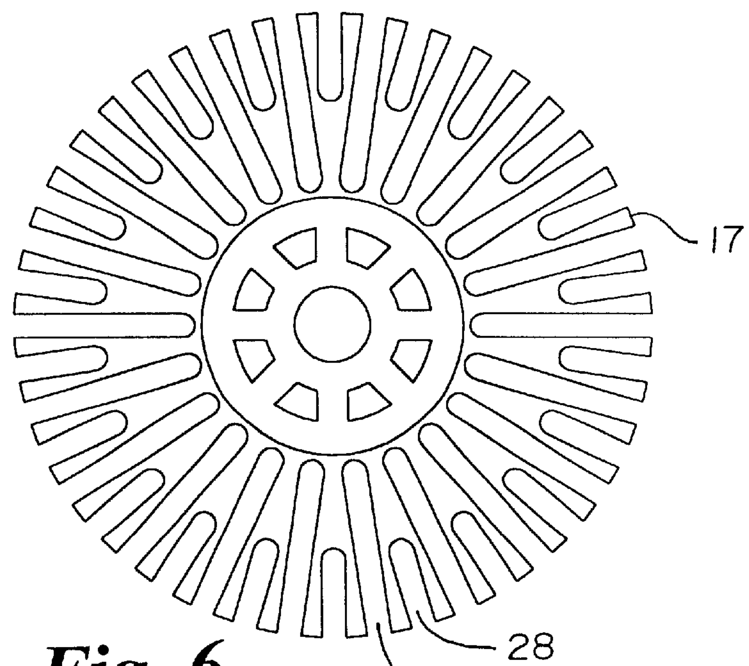
FIG. 5 and FIG. 6 are end views of winding disks showing alternative fin designs.

FIG. 5 shows an end view of a winding disk having a two-layer fin design. The design utilizes the added thickness at the peripheral edge of the fin to accommodate an additional secondary notch 28. Secondary notches 28 have a larger inner diameter than primary notches 27 but the same outer diameter. Therefore, secondary notches 28 will hold fewer layers of tube than primary notches 27. Preferably, the thickness of the fins is no less than 0.02 inches for application in cardioplegia heat exchangers.

During winding of the two-layer fin design, initially only the primary notches are wound. After the layer of tube in the primary notches reaches the inner diameter of the secondary notches, the tube is wound into both the primary notches and the secondary notches. At this point a transition layer is reached. The transition layer being the first layer in which tubes are wound into both the primary and secondary notches. At the transition layer the core rotating means halves the incrementing angle of the winding core. Halving the incrementing angle allows the winding apparatus to place a row of tubing in both the primary and the secondary notches. Winding continues until the layers reach the outer diameter of the notches.

The two-layer fin design doubles the number and density of tubes when the tube is being wound into both the primary and the secondary notches relative to number and density of the one-layer fin design. Thereby, the two-layer fin design provides for more efficient utilization of space. The increased efficiency means more tubes are wound into less volume, which increases the thermal conductive contact surface area and therefore increases the thermal efficiency of a heat exchange device or the gas exchange efficiency, if the bundle is for use in an oxygenator. It also allows a transfer device using the tube bundle to have a smaller priming volume because the transfer device's outside diameter can be smaller, important for most medical device applications.

Using the two-layer fin design, a winding core for a cardioplegia heat exchanger having winding disks with an outer notch diameter of 1.15 inches, an inner primary notch diameter of 0.47 inches and using 0.040 inch diameter polyurethane tubing can have eight layers. The primary notches can be wound with 22 rows for the first four layers. The following four layers have 44 rows because of the combined primary and secondary notches. Using these parameters, a total of 264 cut tubes will be in the final tube bundle.

Figure 6:
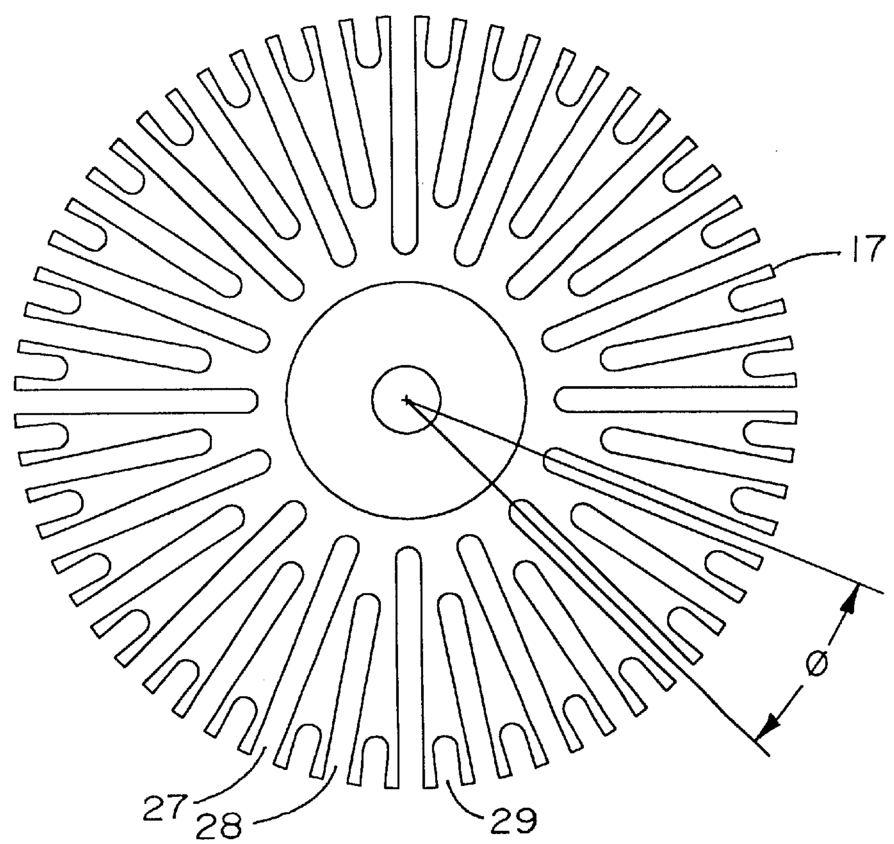

FIG. 6 shows an end view of the winding disk having a three-layer fin design. The three-layer fin design utilizes the remaining thickness at the peripheral edge of the fin from the two-layer fin design of FIG. 5 to accommodate an additional tertiary notch 29. Thereby, the three-layer fin design incorporates primary notches 27 and secondary notches 28 of the two-layer fin design and adds tertiary notches 29 between primary notches 27 and secondary notches 28. Secondary notches 28 have an inner diameter greater than primary notches 27 and tertiary notches 29 have an inner diameter greater than secondary notches 28. Therefore, secondary notches 28 will hold fewer layers of tube than primary notches 27 and tertiary notches 29 will hold fewer layers of tube than secondary notches 28. Preferably, the thickness of the fins is no less than 0.02 inches for application in cardioplegia heat exchangers.

During winding the three-layer fin design tube is initially wound only in the primary notches. After the layers of tube in the primary notches reach the inner diameter of the secondary notches the tube is wound into both the primary and the secondary notches. At this point a first transition layer is reached. The first transition layer is defined as the first layer in which tubes are wound into both the primary and secondary notches. At the first transition layer the core rotating means halves the incrementing angle of the winding core. Thereby, the winding apparatus places rows of tubing in both the primary and secondary notches. Winding then continues until the layers of tube in the primary and secondary notches reach the inner diameter of the tertiary notches. At this point a second transition layer is reached. The second transition layer being the first layer in which tubes are wound into both the primary, secondary and tertiary notches. At the second transition layer the core rotating means again halves the incrementing angle of the winding core. Thereby, the winding apparatus places tubing in the primary, secondary and tertiary notches. Winding then continues until the layers of tubing reach the outer diameter of the notches. The three-layer fin design, like the two-layer fin design, doubles the number of rows and halves the incrementing angles at each transition layer. Thereby, the three-layer fin design allows more tubes to be wound into a tighter volume, which again increases the thermal contact surface areas and therefore increases the thermal efficiency of the transfer device when the bundle is used as a heat exchanger. Thus, the three-layer fin design results in a transfer device with even smaller priming volume than the single fin design or the double layer fin design.

Using the three-layer fin design, a winding core for a cardioplegia heat exchanger having winding disks with an outer diameter of 1.40 inches, an inner diameter of 0.54 inches and using 0.040 inch diameter polyurethane tubing can have ten layers. The primary notches can be wound with 16 rows for the first four layers. The following four layers have 32 rows because of the combined primary and secondary notches. The last two layers have 64 rows because of the combined primary, secondary and tertiary notches. Using these parameters, a total of 352 cut tubes will be in the final tube bundle.

Figure 7:
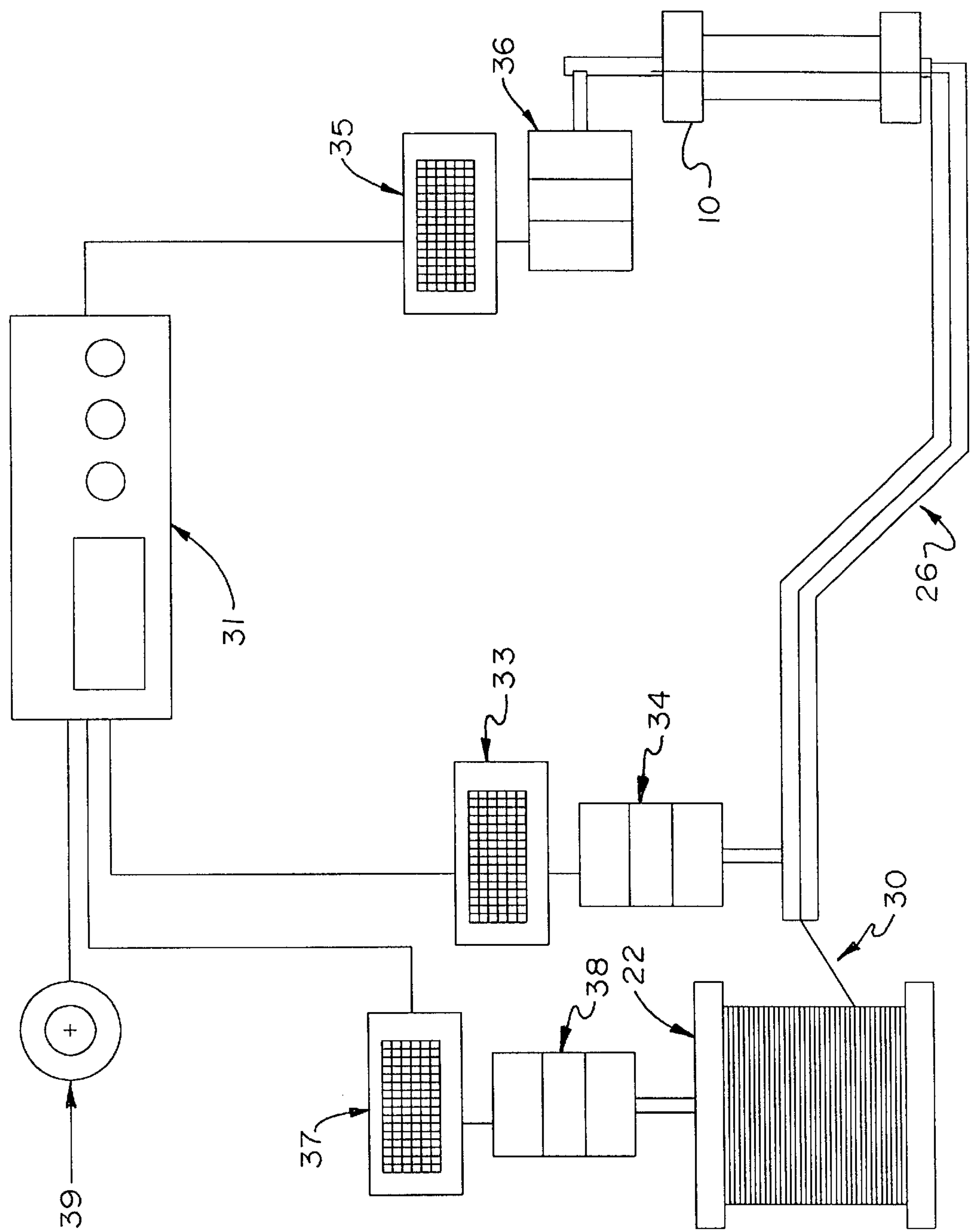
FIG. 7 is a schematic diagram of an embodiment of a computer controlled winding apparatus in accordance with the present invention.

The winding apparatus can additionally include a computer control, schematically represented in FIG. 7. The computer control regulates the core rotating means and the shuttle rotating means. In the embodiment of FIG. 7, the computer control includes a computer 31, shuttle stepper drive 33, a shuttle stepper motor 34, a core stepper drive 33, and a core stepper motor 34. Tube bobbin 22 can also be provided with a bobbin stepper drive 37 and a bobbin stepper motor 38. Computer 31 is connected to the stepper drives. The computer executes the winding software and issues commands to the stepper drives regarding when each motor is to activate. The stepper drives are connected to the stepper motors. The stepper drives then initiate the proper angular displacement of the stepper motors. Stepper motors are preferred because their rotation can be precisely controlled, ensuring an accurate winding pattern at high speeds. For example, if 22 degree incrementing angle is required lay tube in subsequent notches on the core, as represented by $\phi$ in FIG. 6, then after one wind of the tube shuttle around the core, the core is rotated 22 degrees. The stepper motor, in this example, is designed such that 22 degrees will be achieved and held accurately. An appropriate sequence of instructions would be as follows:

1. a command to rotate 22 degrees is issued by the software in computer 31 to core stepper drive 35;
2. core stepper drive 35 controls core stepper motor 76 to rotate 22 degrees;
3. a command to rotate 360 degrees is issued by the software in computer 31 to shuttle stepper drive 33; and
4. shuttle stepper drive 33 controls shuttle stepper motor 34 to rotate 360 degrees.

The process then repeats until the winding is complete. The software will control the timing, incrementing angles and number of passes around the core in order to control the bundle's winding pattern. The software can be implemented such that an external potentiometer 39 can control the rate of the winding process from its connection to computer 31. The software can also be written to allow the changing of variables, such as the total number of winds around core 10 and the angular displacement from one row to the next. The software can also adjust the winding so as to recognize and adjust for transition layers for cores with finned disks having secondary and tertiary notches. This will allow winding apparatus 1 to create bundles of many different sizes and patterns. In a preferred embodiment, computer 31 implements a bundle design with the fewest variable changes.

In operation of winding apparatus 1, tube 30 is routed from bobbin 22 through tube shuttle 26 and is secured to winding core 10. Tube 30 is preferably secured such that the end of tube 30 is not located between the two winding disks. Tube 30 can be secured to winding core 10 using an adhesive, tying or by other means well-known to those skilled in the art. Shuttle rotating means 28 rotates the shuttle around the winding disks of winding core 10. Tube shuttle 26 thereby guides tube 30 around the first winding disk 14 and the second winding disk 16 of winding core 10. Each cycle is one complete revolution of shuttle 26 around winding core 10. Each cycle results in two rows of tube being wound on winding core 10. After each complete cycle around core 10, core rotating means 20 rotates core 10 an appropriate incrementing angle such that the adjacent row can be wound onto the layer. The incrementing angle being the degree of rotation of core 10 required to align tube shuttle 26 with core 10 such that the next rows wound will be adjacent to the prior row. When a finned winding core is used, core 10 is aligned and the incrementing angle chosen so as to maintain alignment between notches 19 and the location at which tube 30 leaves tube shuttle 26. The cycle is generally repeated until the rows extend around the periphery of winding core 10 completing the layer, although this may vary depending on winding pattern. A second layer is then added on the outside circumference of the first layer and so on.

Figure 8A:
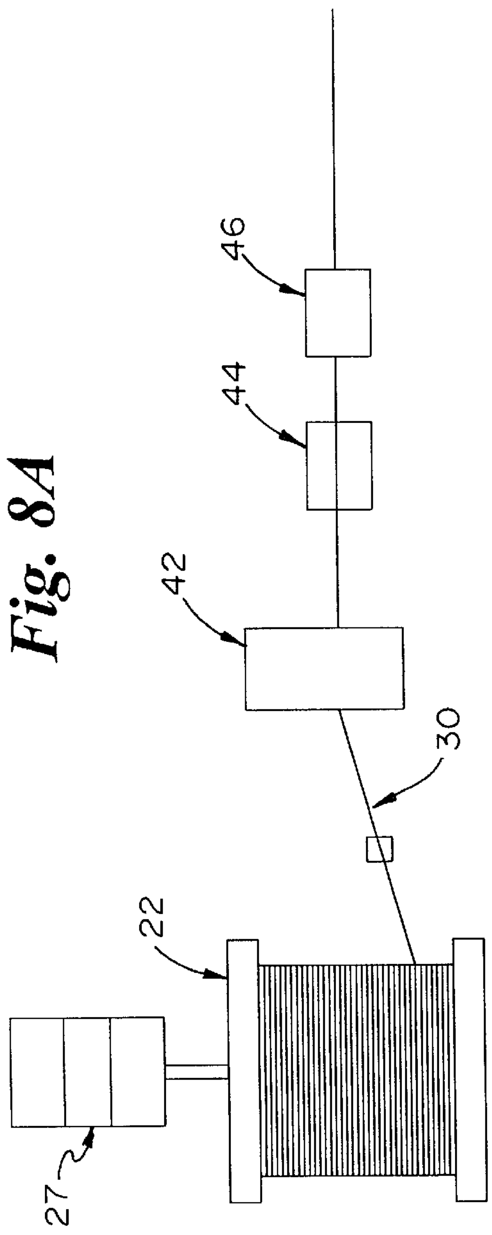
FIGS. 8A and 8B are a side view and a top view, respectively, of an embodiment of a bobbin tension means.
Figure 8B:
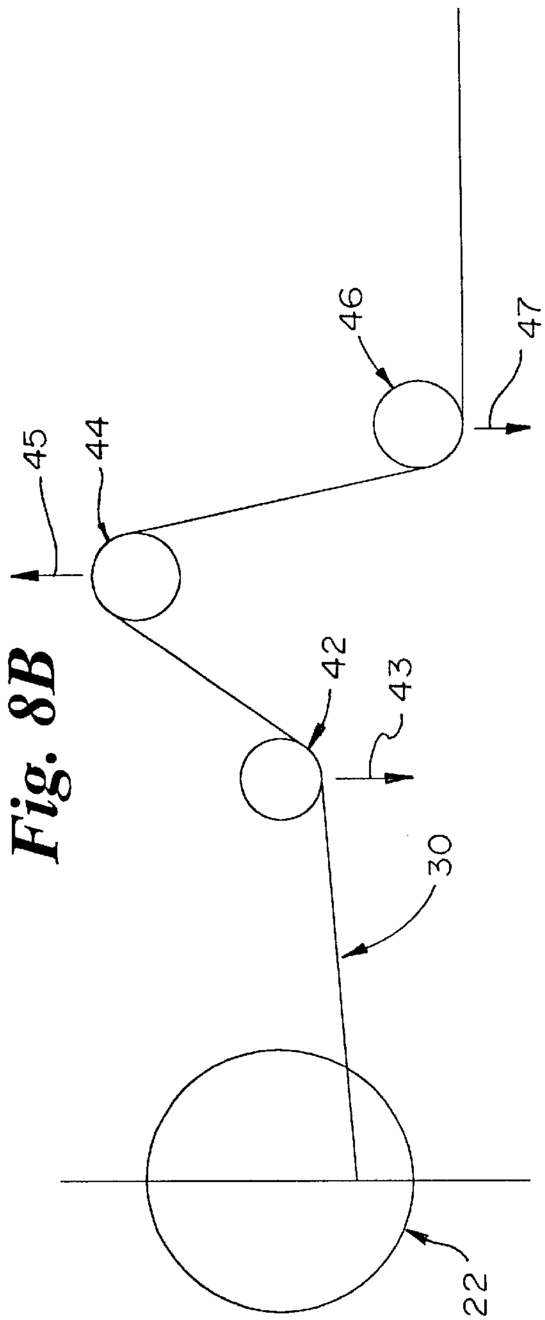

When a polyurethane tube is used for winding the tube can be tacky and self-adhere as it comes off the bobbin which can lead to inconsistent tension in the wound tube. Inconsistent tension creates slack in the tube line between the bobbin and winding core, which increases the risk of the tubing tearing, stretching out of shape, or snapping during winding. Thus, the winding apparatus can additionally include a means for applying substantially constant tension to the tube as the tube is drawn from the bobbin. The tension means provides the further benefit of removing kinks in the lumen as the tube is removed from the bobbin. The tension means includes at least one pulley around which tube 30 is wound. An embodiment of the tension means is shown in FIGS. 8A and 8B. FIG. 8A provides a top view and FIG. 8B provides a side view of an embodiment of the tension means. Tension means 80 of FIGS. 8A and 8B include a bobbin motor 27, a first pulley 42, a second pulley 44 and a third pulley 46. The tubing is wound from bobbin 22 around first pulley 42, second pulley 44 and third pulley 46 and then through to the tube shuttle, not shown. During subsequent winding, the rate of tube output from the bobbin motor is slightly slower than the rate at which tube is being wound onto the core. The difference in rates generates a tension on the tube. The pulleys are movably mounted and are biased by springs in the direction of first arrow 43, second arrow 45 and third arrow 47 for first pulley 42, second pulley 44 and third pulley 46, respectively. The movement of the tension pulleys compensates for the sticking tubes by taking up the slack from the release of a tube stuck on the bobbin. During winding, the pulleys are displaced by the tension created by motor 27 and the tube shuttle and confer a generally constant tension over a distance proportional to the pulleys displacement. The amount of displacement depends on the length and spring constant for each spring. Thereby, the tension pulleys maintain a substantially constant tension even when the tube sticks to the bobbin.

Figure 9A:
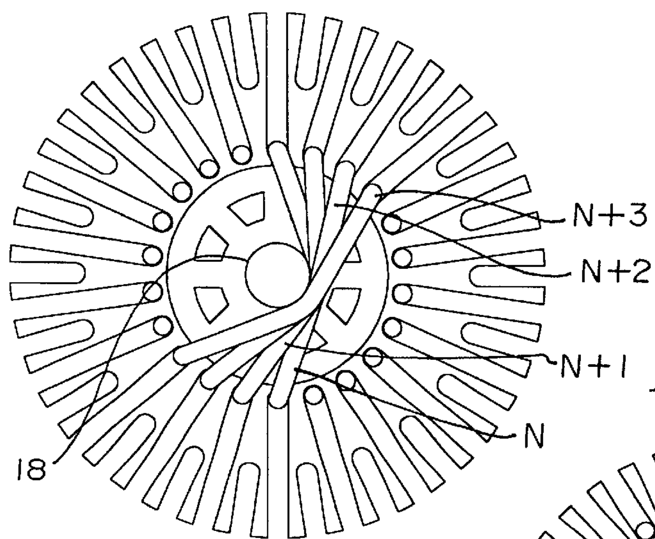
FIGS. 9A, 9B and 9C are a top views illustrating consecutive winding patterns of the tubes as they are wound about a winding core having winding disks as shown in FIG. 5.

The winding pattern can vary depending on whether the fiber bundle is going to be used in a heat exchanger, dialyzer or oxygenator. In an embodiment used for a cardioplegia heat exchanger, the bundle is wound straight across each winding disk of the core such that the tube is wound from a notch on one side of the core to a diametrically opposing notch, as shown in FIG. 9A. The first row deposited is wind row n. The wind rows in the pattern of FIG. 9A are deposited in diametrically opposing notches. This results in the tube being angled around and biased against winding pin 18. This represents the shortest distance from one side of the core to the other, and therefore minimizes the amount of tube thrown away after the winding disks are potted and cut. After row n is deposited the core is rotated by an incrementing angle counter-clockwise such that the tube shuttle is aligned to wind tube into wind row n+1. As the cycles continue, the layers build up to form a dome, shown in FIG. 13, around the winding pin at each end. At about the fourth to sixth layer, the dome reaches a size and angle where surface contact friction is no longer sufficient to keep the outer tube layers from slipping on the tube domes.

Figure 9B:
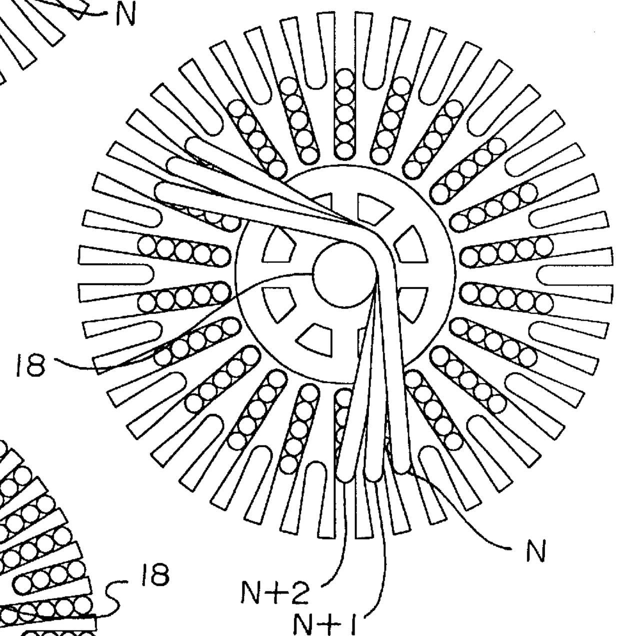
Figure 9C:
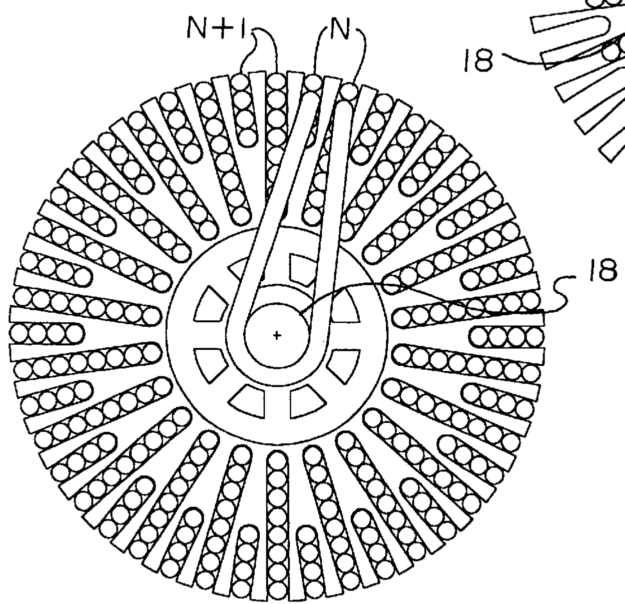

Typically, when more than four to six layers are required the winding pattern should be altered to avoid the tube's slipping, although, the layer at which the pattern changes will depend on many variables, including the core design, tube size, tube material, tension applied, as well as other variables recognized by those skilled in the art. An example of how the winding pattern can be altered is shown in FIG. 9B. For exemplary purposes, the winding pattern in FIG. 9B changes after the fourth layer. The pattern of FIG. 9B uses the winding pin to prevent the tube from slipping off of the dome. The tube is angled around the winding pin thus biasing the tubing against the pin and preventing the tube from sliding off the dome. For illustrative purposes only, in FIG. 9B the winding pattern change was made at the transition layer. In FIG. 9B, the transition layer is the point where the tube count increased from 22 rows per layer up to 44 rows per layer. The alteration in winding shown in FIG. 9B rotates the tube counter-clockwise six notches (numbered 1 to 6) to prevent the tube from slipping off the dome. This winding pattern results in twelve notches (numbered 1 to 6 and 1' to 6') without rows of tube when the subsequent layer is started and twelve notches without tube upon completion of winding. Depending on the application for the tube bundle, it may be possible to keep the last few notches open on the last row, since a few tubes left out of the wind will not have a significant impact on the device's heat exchange performance. Alternatively, the winding pattern can be altered to a third configuration, as shown in FIG. 9C, to fill the notches left without tubes after completing the pattern shown in FIG. 9B. The winding pattern of FIG. 9C rotates the core one increment less than 360 degrees such that the tubing makes a 180 degree turn around the winding pin. Thus, adjacent rows are filled with rows of tubing until all the notches have a row of tube. This is exemplified in FIG. 9C as wind row n and wind row n+1 are deposited around the core wherein each wind row deposits two rows of tube.

Figure 10:
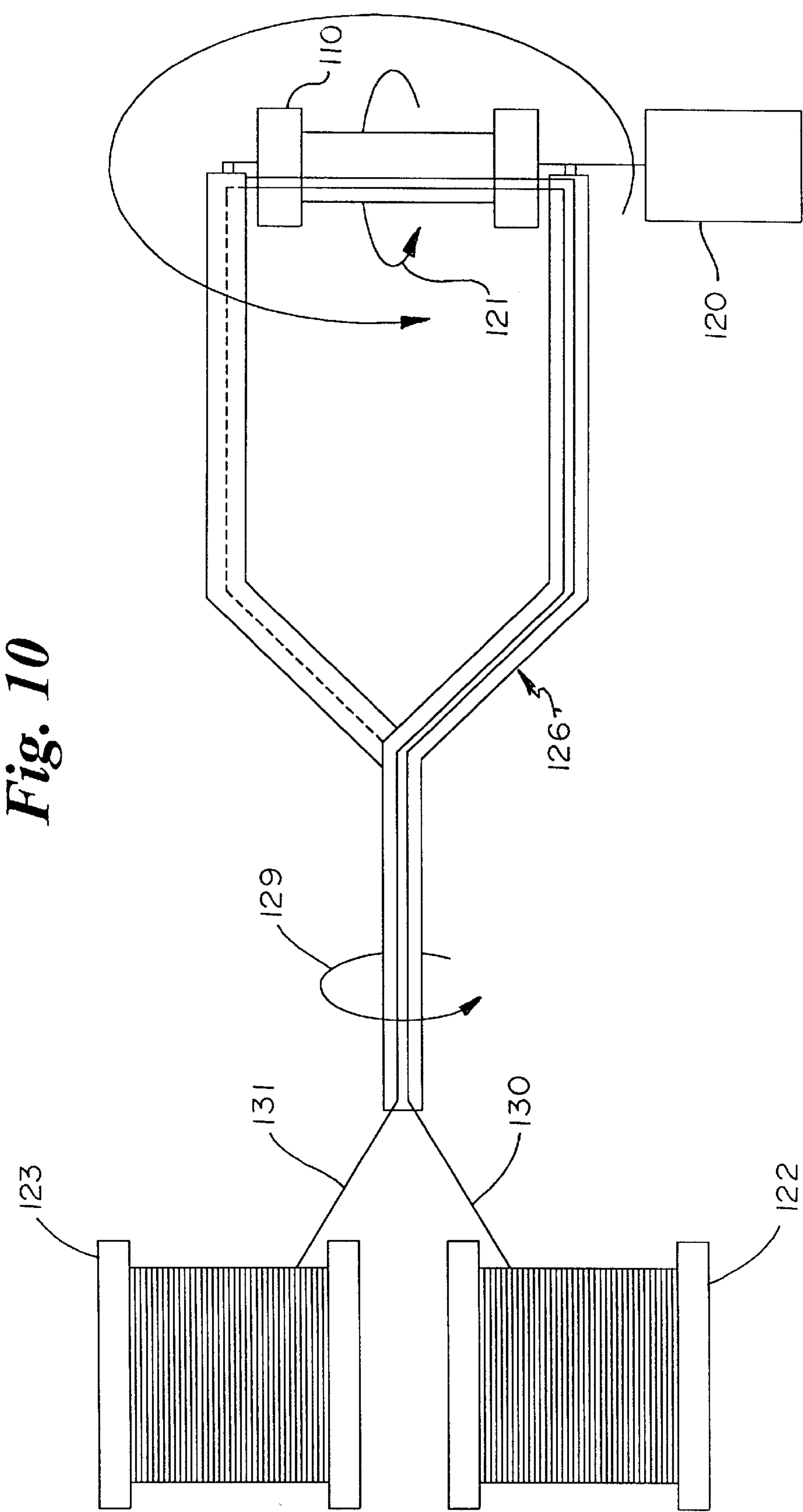
FIG. 10 is a schematic diagram of an alternative embodiment of the winding apparatus having two bobbins.

In another embodiment of the winding apparatus shown in FIG. 10, the winding apparatus utilizes two bobbins simultaneously. This embodiment of the winding apparatus includes: a winding core 110; a core rotating means 120 rotating core 110 in the direction of arrow 121; a first tube bobbin 122 holding a first tube 130; a second tube bobbin 123 holding a second tube 131; a tube shuttle 126 which simultaneously guides first tube 130 and second tube 131 around core 110 in the direction of arrow 129; and a shuttle rotating means 128 for rotating the shuttle around core 110. First tube bobbin 122 and second tube bobbin 123 are rotatably mounted such that a length of tubing can be drawn off of the bobbins. First bobbin 122 and second bobbin 123 can be attached to a stepper motor and stepper driver such that the rotation of the bobbins is coordinated by the computer control. First tube 130 and second tube 131 may be composed of any biocompatible material flexible enough to withstand winding but the tubes are typically polyurethane for heat exchanger applications. First tube 130 and second tube 131 may have an outside diameter of 0.01 to 0.10 inch and a wall thickness of 0.001 to 0.050 but preferably has an outside diameter of 0.03 inches to 0.045 inches and a wall thickness of 0.002 inches and 0.005 inches for cardioplegia heat exchanger applications. Tube shuttle 126 accepts first tube 130 and second tube 131 from first bobbin 122 and second bobbin 123, respectively. As tube shuttle 126 rotates around winding core 110 first tube 130 and second tube 131 are draw from their respective bobbins and wound end over end onto winding core 110, as shown in FIG. 10. In this embodiment, the tube shuttle must align the tubing so as to distribute first tube 130 and second tube 131 in adjacent rows on winding core 110. Furthermore, winding core 110 must have an even number of notches. The winding apparatus pulls tubes from the two separate bobbins and winds it onto the core. Core rotating means 120 incrementally rotates core 110 on an axis substantially parallel to and in the same plane as the tubing shuttle's rotational axis so the rows of tube 130 and tube 131 are evenly distributed onto each layer wound around core 110. In this embodiment, twice as much tube can be wound onto the core than with the embodiment shown in FIG. 1.

In another embodiment, not shown, a bobbin wound with two or more tubes can be used to wind multiple tubes simultaneously. The tubes must be extruded continuously and placed onto the bobbin such that the winding apparatus can draw the tubes off the bobbin at the same time. This embodiment requires a shuttle designed to distribute the two or more tubes onto a core. Further, the embodiment requires the addition of a comb to separate the tubes before winding onto the core.

Figure 11:
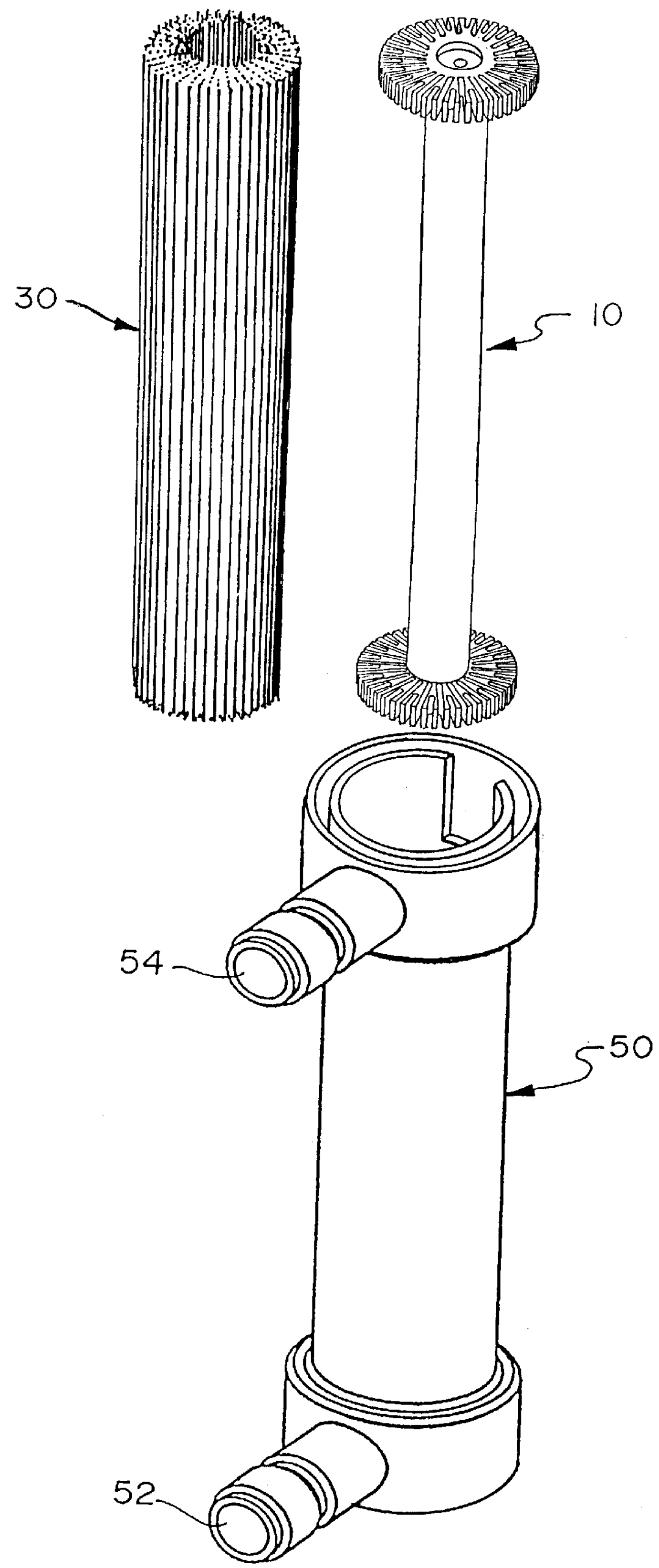
FIG. 11 is an exploded diagram of a heat exchange device having a wound tubular bundle manufactured in accordance with the present invention.

After winding, the tube bundle is removed from the winding apparatus and the bundle assembly is placed into a housing 50 shaped to accept the bundle. Housing 50 typically includes a fluid inlet 52 and a fluid outlet 54 configured so as to allow a fluid to pass through housing 50 and contact the outer surface of tubes 30. An exploded embodiment of housing 50 including a potted fiber bundle is shown in FIG. 11. Housing 50 is designed to accept the wound bundle and function as a transfer device. The wound bundle may be slightly oversized or undersized to fit within the housing as required by the application. In a preferred embodiment, the bundle is oversized by at least 0.003 inches to prevent fluid shunting that could affect the transfer device's performance, particularly in mass transfer devices. Although for heat exchanger applications, such over-sizing is not necessary because fluid shunting does not significantly affect the transfer device's performance.

The wound bundle is potted at both ends within housing 50. The potting material is deposited within housing 50 defining a sealed fluid flow path between fluid inlet 52, housing 50 and the tubes' outer surface, and fluid outlet 94. The potting material is preferably a thermoset polyurethane compound or similar material. In defining the sealed fluid flow path, the potting material further provides a barrier between the trans-lumenal space, through the lumen of the tubes, and the sealed fluid flow path, external to the tubes. In a heat exchanger for a blood cardioplegia device, the potting material separates the water path, analogous to the sealed fluid flow path, from the blood path, analogous to the trans-lumenal space. Additionally, the potting material functions to secure the bundle within the housing.

Figure 12:
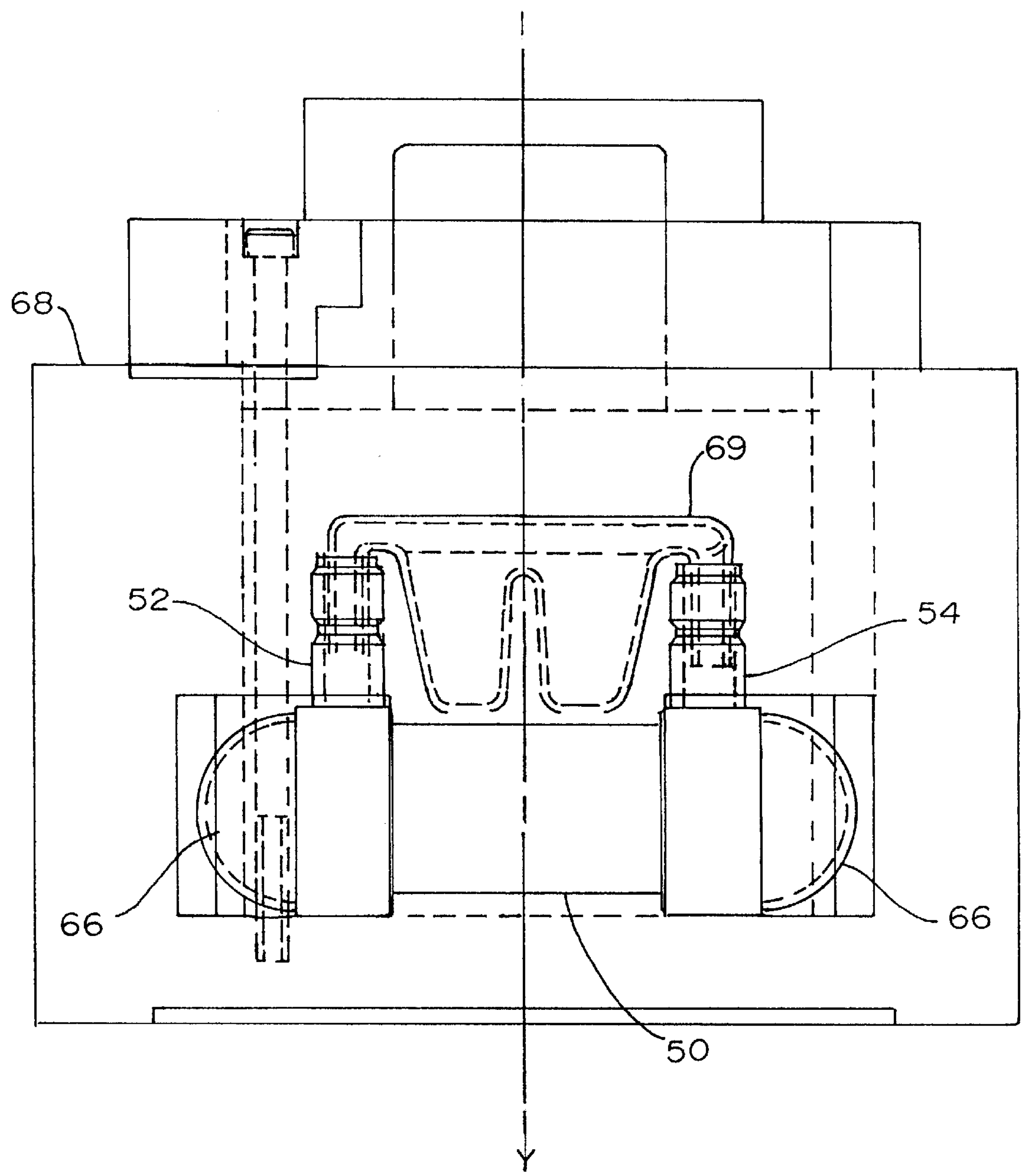
FIG. 12 is a cross-section of an embodiment of the centrifuge rotor used during potting of the tube bundles.

The wound bundle is preferably potted at both ends simultaneously using a centrifuge, as shown in FIG. 12. Simultaneous potting reduces the time required to produce the fiber bundles because a single curing period can be used instead of separate periods for the first and second ends of the bundle. Both ends are potted simultaneously by installing potting caps 66 over each open end of the housing containing the fiber bundle. Potting caps 66 form a seal over the ends of housing 50 preventing the potting material from leaking during curing. Potting caps 66 are preferably made from or coated with a hydrophobic material such as polypropylene, polyethylene or PTFE. The hydrophobic material prevents the urethane potting material from adhering to the potting caps. Housing 50 is mounted in a rotor 68 as shown in FIG. 12. The rotor is then mounted in the centrifuge such that housing 50 spins around an axis Y so as to force potting material into end caps 66. In the embodiment of FIG. 12, the potting material is supplied from a potting cup 69 which utilizes centripetal force generated by the centrifuge to pull potting material out of cup 69 and into end caps 66 on housing 50. Thus, the potting material is directed from the cup 69 into end caps 66 through inlet 52 and outlet 54 of housing 50. Alternatively, the potting material can be directed from the cup 69 into end caps 66 through tubes, not shown, connecting potting cup 69 to end caps 66. Housing 50, the wound bundle, end caps 66 and potting cup 69 are centrifuged at a rate sufficient to force the potting materials to the ends of the housing and remove any entrapped bubbles. Typically, the force applied is between 100 times and 220 times the force of gravity. Preferably, the centrifuge is maintained at a temperature above 25 degrees Celsius to expedite curing. The centrifuge is run for between 15 to 60 minutes depending on the time required for the urethane to set up enough for safe handling. This force ensures the urethane will penetrate the bundle completely, adhere to the surfaces of tubes 30, housing 50 and winding core 10, and prevent micro-bubbles from forming due to the off gassing while the urethane cures. After centrifugation the materials are further cured at 40 degrees Celsius for a minimum of 13 hours. After curing, potting caps 66 are removed exposing the potted ends of the device.

Figure 13A:
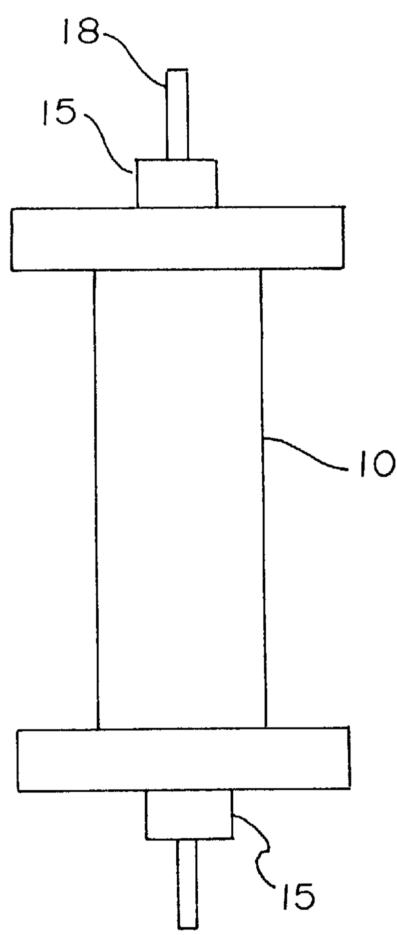
FIGS. 13A and 13B are side views of a winding core with tube and without tube, respectively.
Figure 13B:
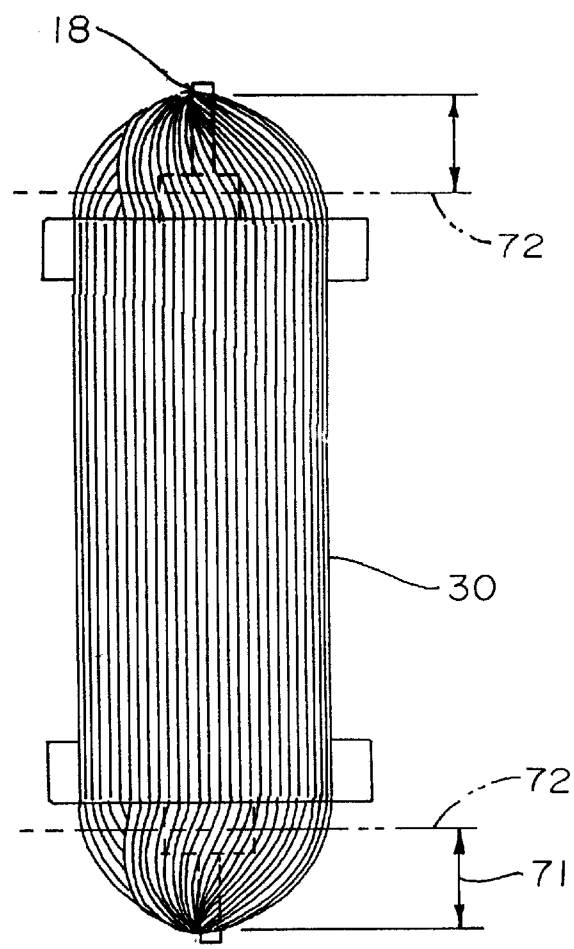

Potted ends 71 are removed with a cross-cut 72 to expose the lumen of the tubes, as shown in FIGS. 13A and 13B. Prior to cutting, the entire assembly may be heated. The heating of the bundle softens the bundle to better facilitate cutting the ends. Cut 72 is made at each end of the device and cuts through the potting material (not shown), tube 30, cutting pad 15 and typically winding pin 18. If winding pin 18 is composed of an uncuttable material then pin 18 must be removed before cutting. Cuts 72 are performed in such a manner that a uniform, flat surface is formed on each end. Cuts 72 are made parallel to the top surface plane of the device. Cuts 72 are made proximal to the creases formed during the winding process. The creases are created at each end of the bundle where the tube bends around cutting pad 15. Therefore, it is desirable to make the cut below the crease in order to insure that the lumen of the tubes are not restricted. Typically, this results in cuts 72 made about 0.033 inches above the top and bottom lip of the housing holding the potted bundle. Cuts 72 are made with a two-sided microtome blade or similar cutting technique. Usually a first rough cut is used to remove a large portion of the material, followed by two or three cuts between 0.001 and 0.005 inches thick to obtain the final, desired surface finish. Cutting in this manner prevents a concave surface from forming which can be undesirable because of poor flow dynamics and possible creation of stagnate areas that might prove thrombogenic to the blood.

In a preferred embodiment, cutting pads 15, tubes and potting material are composed of the same material. Typically, the material will be polyurethane. Using the same material facilitates uniform deformation and shear resistance through the process of cutting. This ensures a relatively flat surface is generated, as opposed to the risk of blade slippage created by cutting through materials of different hardness and the waviness in the cut surface which can result. A typical uniform hardness such as shore 65D will insure a flat surface is made during the cutting process.

Figure 14:
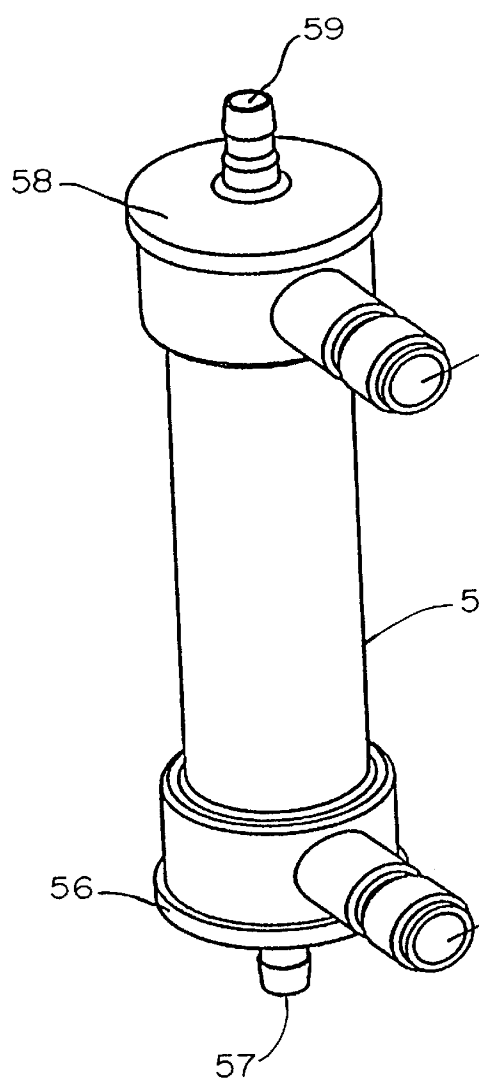
FIG. 14 is an isometric view of a housing having end caps secured over the lumen of the cut tubes.

After cutting, the bundle within the housing is configured for a particular application. For use as a heat exchanger, end caps are placed over the cut ends of the bundle within the housing. FIG. 14 shows a typical configuration for a housing 50 containing a wound tube bundle for use as a cardioplegia heat exchanger. A first end cap 56 is secured over the first end of housing 50. First end cap 56 has a fluid inlet 57 configured to communicate fluid from the fluid inlet to the lumen of the potted tubes when secured to housing 50. A second end cap 58 is secured over the second end of housing 50. Second end cap 58 has a fluid outlet 59 configured to receive fluid from the lumen of the potted tubes when secured to housing 50. The end caps are typically secured to the housing using an adhesive. Alternatively, the end caps can be secured to the housing by sealedly interlocking with the housing. To interlock the end caps and housing, the end caps and housing can be molded such that the housing is threaded and the end caps shaped to receive the threads of the housing or vice-versa. Fluid inlet 57 and fluid outlet 59 can be further configured to connect to the tubing of a cardioplegia circuit.

Figure 15:
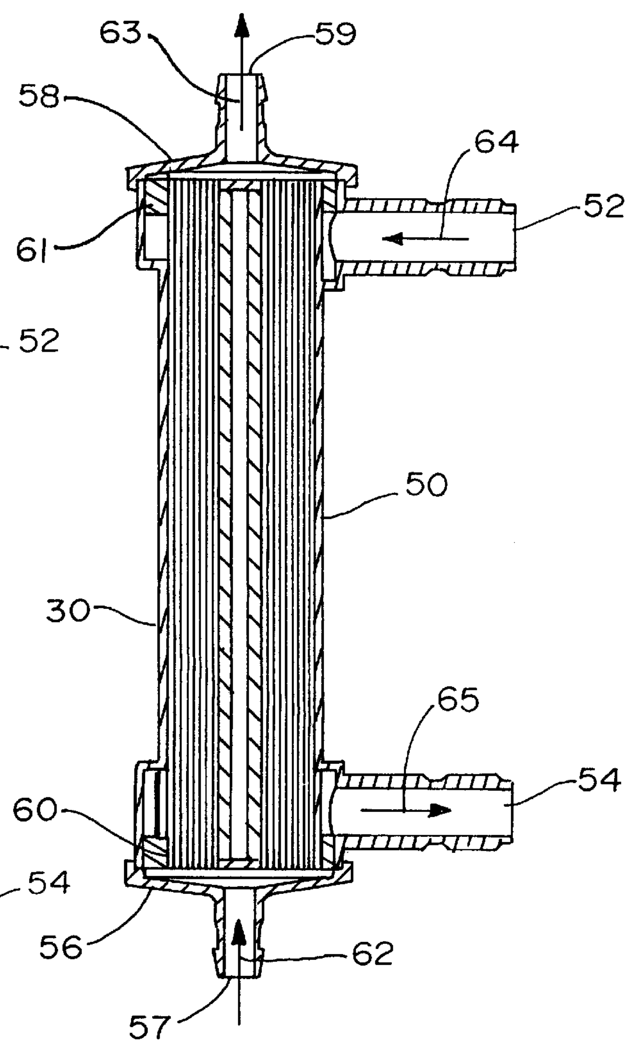
FIG. 15 is a vertical cross-section of the device of FIG. 14.

FIG. 15 is a detailed cross-section of the assembled first end of the cardioplegia heat exchanger of FIG. 14. In operation, fluid inlet 57 and fluid outlet 59 are connected to tubing designed to communicate a blood cardioplegia set to a patient. Inlet 52 is connected to a source of heat exchange fluid and outlet 54 is connected to a return reservoir for the heat exchange fluid. First end cap 56 receives a cardioplegia fluid and communicates the cardioplegia fluid to the lumen of tubes 30. Potting material 60 at the first end of housing 50 prevents the entering cardioplegia fluid from contacting the extra-luminal space between tubes 30. The cardioplegia fluid passes through the length of tubes 30 and is received by second end cap 58. Potting material 61 at the second end of housing 50 prevents the exiting cardioplegia fluid from contacting the extra-lumenal space. End cap 58 communicates with the cardioplegia fluid through outlet 59. Simultaneously, a heat exchange medium enters the housing through inlet 52 and is directed by housing 50 and potting material 61 into the extra-lumenal space. As the heat exchange medium flows through the extra-lumenal space, the heat exchange medium comes into contact with the outer surface of tubes 30. The contact exchanges energy in the form of heat between the heat exchange medium and tubes 30. The tubes then exchange energy with the cardioplegia fluid. Thus, the contact of the heat exchange medium with the outer surface of tubes 30 creates a heat exchange relationship between the heat exchange medium and the cardioplegia fluid. The heat exchange medium flows through the housing until potting material 60 and the housing guides the fluid through outlet 54.

The bundle formed in the above-described embodiments is suitable for use as a heat exchanger in a blood cardioplegia circuit and the dimensions, tubing, surface area, and other particulars are suitable therefore. As mentioned previously, the method and winding apparatus of the present invention can also be used to make tube bundles for applications such as blood oxygenators or hemoconcentrators that utilize a mass transfer device.

If the instant method and apparatus is used to make a blood oxygenator, more tubing surface area is necessary than in the embodiments for use as a heat exchanger. Typically, blood oxygenator mass transfer devices can have as little as 1.8 square meters of surface area. The tubes used in oxygenators typically have a diameter of between 0.018 to 0.022 inches. The tubes typically have a nominal wall thickness of 0.03 to 0.20 micrometers and a porosity of about 40%. Given these dimensions, an oxygenator bundle with a surface area of 1.8 square meters would include about 14,800 fibers is the bundle were about 6 inches in length. This results in a bundle diameter of approximately 2 to 5 inches, depending on the notch design chosen. The smaller diameter of this design translates into a lower priming volume and therefore less hemodilution. Typically, in such applications, the path of blood flow would be exterior to the hollow fibers or tubes making up the bundle.

Similar specifications can be used for polymer based hemoconcentrators and dialyzers. The tube used for these applications is typically a polymer which may be a cellulose based polymer or a synthetic polymer. The cellulose tube material used can include cuprammonium rayon, viscose rayon and cellulose acetate. The synthetic tube material used can include polyvinyl alcohol, ethylene vinyl alcohol, polysulfone, polypropylene or polymethyl-methacrylate. The tube is usually 200 $\mu$m to 300 $\mu$m in diameter with a wall thickness of 5 $\mu$m to 20 $\mu$m. The overall configuration for hemoconcentrators and dialyzers are the generally the same as described above for heat exchangers. Specifically, hemoconcentrators and dialyzers can have a similar geometries, similar number of tubes and similar surface areas. Typically, the blood flow within the hemoconcentrator or dialyzer is through the tubes' lumen and dialysis solution or saline runs over the outer surface of the tubes.

What is claimed is:

1. A transfer device, comprising:

a wound tube bundle having a plurality of tubes having an outer surface and a lumen wound around a winding core, the winding core having a body, a first winding disk and a second winding disk, the first winding disk attached to a first end of the body and the second winding disk attached to a second end of the body, the first and second winding disks having a peripheral edge and a central axis that substantially coincides with a longitudinal axis of the winding core, the first and second winding disks further having a plurality of fins extending from the peripheral edge towards the central axis, the fins defining a plurality of primary notches securing the plurality of tubes;

a housing having a first end and a second end surrounding the wound tube bundle;

a potting material disposed at the first and second ends of the housing sealing the first and second ends of the winding core to the tube and the housing wherein the potting material, the outer surface of the tubes and the housing form a first fluid chamber;

a first fluid inlet communicating with the first fluid chamber;

a first fluid outlet communicating with the first fluid chamber;

a second fluid inlet communicating with the lumen of the plurality of tubes at the first end of the housing; and a second fluid outlet communicating with the lumen of the plurality of tubes at the second end of the housing.

2. A transfer device, as in claim 1, wherein the fins further define a plurality of secondary notches shaped to receive tube from the tube shuttle, the primary and secondary notches each having a length as measured from the peripheral edge towards the central axis, the length of the primary notches being greater than the length of the secondary notches.

3. A transfer device, as in claim 1, wherein the fins further define a plurality of tertiary notches shaped to receive tube from the tube shuttle, the tertiary notches having a length as measured from the peripheral edge towards the central axis, the length of the tertiary notches being less than the length of the secondary notches.

4. A transfer device, as in claim 1, wherein the tube is polyurethane.

5. A transfer device, as in claim 1, wherein the tube is a polymer material selected from the group of cuprammonium rayon, viscose rayon or cellulose acetate.

6. A transfer device, as in claim 1, wherein the tube is a polymer material selected from the group of polyvinyl alcohol, ethylene vinyl alcohol, polysulfone, polypropylene or polymethyl-methacrylate.

7. A transfer device, as in claim 1, wherein the tube is a microporous membrane hollow fiber.

8. A transfer device, as in claim 1, wherein the winding core further comprising a first cutting pad attached to the first winding disk and a second cutting pad secured to the second winding disk.

9. A transfer device, comprising:

a wound tube bundle having a plurality of tubes having an outer surface and a lumen wound around a winding core, the winding core having a body, a first winding disk and a second winding disk, the first winding disk attached to a first end of the body and the second winding disk attached to a second end of the body, the first and second winding disks having a diameter greater than a diameter of the body such that the tube wound onto the winding core forms a space between the diameter of the body and the diameter of the first and second winding disks;

a housing having a first end and a second end surrounding the wound tube bundle;

a potting material disposed at the first and second ends of the housing sealing the first and second ends of the winding core to the tube and the housing wherein the potting material, the outer surface of the tubes and the housing form a first fluid chamber;

a first fluid inlet communicating with the first fluid chamber;

a first fluid outlet communicating with the first fluid chamber;

a second fluid inlet communicating with the lumen of the plurality of tubes at the first end of the housing; and a second fluid outlet communicating with the lumen of the plurality of tubes at the second end of the housing.

10. A transfer device, as in claim 9, wherein the tube is polyurethane.

11. A transfer device, as in claim 9, wherein the tube is a polymer material selected from the group of cuprammonium rayon, viscose rayon or cellulose acetate.

12. A transfer device, as in claim 9, wherein the tube is a polymer material selected from the group of polyvinyl alcohol, ethylene vinyl alcohol, polysulfone, polypropylene or polymethyl-methacrylate.

13. A transfer device, as in claim 9, wherein the tube is a microporous membrane hollow fiber.

14. A transfer device, as in claim 9, further comprising a first cutting pad secured to the first winding disk and a second cutting pad secured to the second winding disk.

* * * * *